United States Patent [19]
MacLean et al.

[11] Patent Number: 5,861,438
[45] Date of Patent: *Jan. 19, 1999

[54] COMBINATION THERAPY TO PREVENT BONE LOSS PARATHYROID HORMONE AND ESTROGEN AGONISTS

[75] Inventors: David B. MacLean, Providence, R.I.; David D. Thompson, Gales Ferry, Conn.

[73] Assignee: Pfizer Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 803,712

[22] Filed: Feb. 21, 1997

Related U.S. Application Data

[60] Provisional application No. 60/012,399 Feb. 28, 1996.

[51] Int. Cl.$^6$ .......................... A61K 38/00; A61K 31/135
[52] U.S. Cl. ................................................ 514/648; 514/12
[58] Field of Search ........................................ 514/12, 648

[56] References Cited

U.S. PATENT DOCUMENTS

| | | | |
|---|---|---|---|
| 5,047,431 | 9/1991 | Schickaneder et al. | 514/648 |
| 5,118,667 | 6/1992 | Adams et al. | 514/12 |
| 5,254,594 | 10/1993 | Niikura et al. | 514/648 |
| 5,384,332 | 1/1995 | Fontana | 514/648 |
| 5,441,986 | 8/1995 | Thompson | 514/648 |
| 5,455,275 | 10/1995 | Fontana | 514/648 |
| 5,550,164 | 8/1996 | Fontana | 514/648 |

FOREIGN PATENT DOCUMENTS 0635270   1/1995   European Pat. Off. ....... A61K 38/29

*Primary Examiner*—Jerome D. Goldberg
*Attorney, Agent, or Firm*—Peter C. Richardson; Gregg C. Benson; Mervin E. Brokke

[57] ABSTRACT

The present invention provides novel methods of inhibiting bone loss comprising administering to a mammal in need of such treatment an effective amount of a compound of formula I

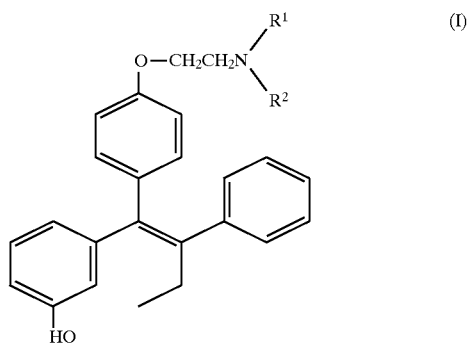

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a hydrogen or a benzyl group; or a pharmaceutically acceptable salt thereof; together with or in combination with parathyroid hormone.

10 Claims, No Drawings

COMBINATION THERAPY TO PREVENT BONE LOSS PARATHYROID HORMONE AND ESTROGEN AGONISTS

This is a continuation of provisional application 60/012,399 filed Feb. 28, 1996, the benefit of which is hereby claimed under 37 C.F.R. §1.78(a)(3).

BACKGROUND OF THE INVENTION

Adams et al., U.S. Pat. No. 5,118,667, disclose the use of bone growth factors in combination with bone resorption inhibitors, either simultaneously in one composition or sequentially, to promote bone formation.

U.S. Pat. No. 5,254,594 claims the use of droloxifene and related compounds to prevent bone loss.

Slovik et al. (J. Bone & Min. Res. 1:377–381, 1986) report the stimulation of bone growth by parathyroid hormone (PTH).

Raloxifene is described in U.S. Pat. No. 4,418,068; in EP-A-584952 it is disclosed that raloxifene is useful in inhibition or prevention of bone loss and in EP-A1-635270 that it is useful in combination with parathyroid hormone to prevent bone loss.

SUMMARY OF THE INVENTION

The present invention relates to methods for inhibiting conditions which present low bone mass comprising administering to a mammal in need of such treatment an effective amount of a compound of formula I

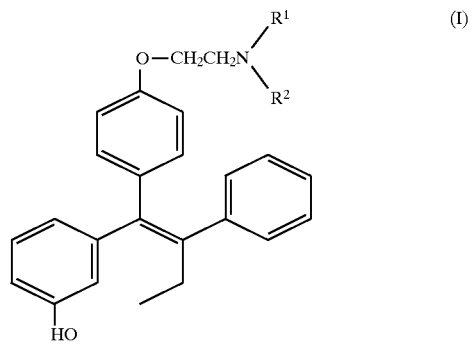

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a benzyl group, or a pharmaceutically acceptable salt thereof; together with or in combination with parathyroid hormone. A preferred compound of formula I is that in which $R^1$ and $R^2$ are methyl. A preferred salt is the citrate salt.

A preferred aspect of this method is wherein the condition which presents with low bone mass is osteoporosis.

Another preferred aspect of this method is wherein a compound of formula I and parathyroid hormone are administered substantially simultaneously.

Another preferred aspect of this method is wherein parathyroid hormone is administered for a period of from about three months to about three years.

Optionally the administration of parathyroid hormone is followed by administration of a compound of formula I for a period of from about three months to about three years without the administration of parathyroid hormone during the second period of from about three months to about three years.

Alternatively, the administration of parathyroid hormone is followed by administration of a compound of formula I for a period greater than about three years without the administration of parathyroid hormone during the greater than about three year period.

In another aspect this invention relates to a kit containing a treatment for a condition which presents low bone mass comprising:

a therapeutically effective amount of a compound of formula I and a pharmaceutically acceptable carrier in a first unit dosage form;

a therapeutically effective amount of parathyroid hormone and a pharmaceutically acceptable carrier in a second unit dosage form; and container means for containing said first and second dosage forms.

DETAILED DESCRIPTION OF THE INVENTION

The present invention concerns methods for inhibiting conditions which present low bone mass. The term "inhibit" is defined to include its generally accepted meaning which includes prophylactically preventing a subject from incurring one or more disease states, holding in check the symptoms of such a disease state, and/or preventing such symptoms. Thus, the present methods include both medical therapeutic and/or prophylactic treatment, as appropriate.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994), Report of a World Health Organization Study Group. World Health Organization Technical Series 843". Childhood idiopathic and primary osteoporosis are also included. Included in the treatment of osteoporosis is the prevention or attenuation of long term complications such as curvature of the spine, loss of height, prosthetic surgery, and prevention of prostate malfunctioning. Also included is increasing the bone fracture healing rate and enhancing the rate of successful bone grafts. Also included is periodontal disease or alveolar bone loss.

The phrase "condition which presents with low bone mass" also refers to a mammal known to have a significantly higher than average chance of developing such diseases as are described above including osteoporosis (e.g., postmenopausal women, men over the age of 60, and persons being treated with drugs known to cause osteoporosis as a side effect (such as glucocorticoid)).

Those skilled in the art will recognize that the term bone mass actually refers to bone mass per unit area which is sometimes (although not strictly correctly) referred to as bone mineral density.

The methods of this invention are practiced by administering to a mammal in need of treatment an effective amount of a compound formula I

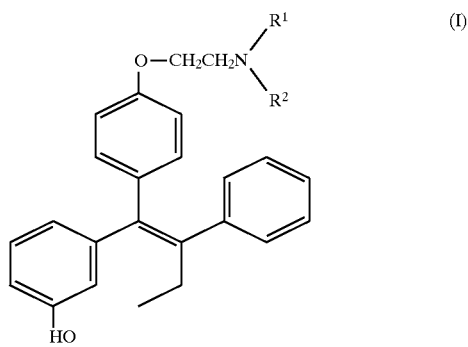

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a hydrogen or a benzyl group; or a pharmaceutically acceptable salt thereof; together with or in combination with parathyroid hormone.

Compounds of formula I are known in the art and essentially are prepared via the methods described in U.S. Pat. No. 5,047,431, which is hereby incorporated herein by reference.

A preferred formula I compound is that in which $R^1$ and $R^2$ each are methyl. This preferred compound is known as droloxifene, (E)-1-[4-(2-Dimethylaminoethoxy)phenyl]-1-(3-hydroxyphenyl)-2-phenylbut-1-ene, which previously has been described as an antiestrogenic agent and is useful for the treatment of hormone dependent mammary tumors (U.S. Pat. No. 5,047,431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be combined with parathyroid hormone (PTH) and administered to an individual in need of treatment for the methods herein described.

For the methods of the present invention, compounds of Formula I and PTH are administered continuously, or from 1 to 4 times daily.

As used herein, the term "effective amount" means an amount of compounds of the methods of the present invention which is capable of inhibiting the symptoms of the pathological conditions herein described. The specific dose of compounds administered according to this invention will, of course, be determined by the particular circumstances surrounding the case including, for example, the compounds administered, the route of administration, the state of being of the patient, and the severity of the pathological condition being treated. A typical daily dose will contain a nontoxic dosage level of from about 0.25 mg to about 100 mg/day of a compound of formula I and about 0.01 mg to 70 mg PTH. Preferred daily doses generally will be from about 1 mg to about 40 mg/day of a compound of formula I and 1 to 40 mg of PTH.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Typically, a formula I compound, or a pharmaceutically acceptable salt thereof, and PTH is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I and parathyroid hormone generally will be administered in a convenient formulation. The following formulation examples only are illustrative and are not intended to limit the scope of the present invention.

In the formulations which follow, "active ingredient" means a compound of formula I, or a salt thereof and parathyroid hormone.

Formulation 1: Gelatin Capsules
Hard gelatin capsules are prepared using the following:

| Ingredient | Quantity (mg/capsule) |
| --- | --- |
| Active Ingredient | 0.25–100 |
| Starch, NF | 0–650 |
| Starch flowable powder | 0–50 |
| Silicone fluid 350 centistrokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 mL) |
| --- | --- |
| Active ingredient | 0.25–100 mg |
| Sodium carboxymethyl cellulose | 50 mg |
| Syrup | 1.25 mg |
| Benzoic acid solution | 0.10 mL |

-continued

Formulation 4: Suspensions

| Ingredient | Quantity (mg/5 mL) |
| --- | --- |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring.

Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
| --- | --- |
| Active ingredient | 20 mg |
| Isotonic saline | 1000 mL |

The solution of the above ingredients is intravenously administered to a patient at a rate of about 1 mL per minute.

When a compound of formula I is referred to, it is understood that it includes salts and solvates thereof. When PTH is referred to, it not only includes the complete human hormone but also includes portions which include the portion of the hormone responsible for bone growth promotion, such as PTH 1-34, and analogs in which the amino acid sequence is modified slightly however, still retaining bone growth promotion properties, such as PTH-RP.

The term "inhibition of bone resorption" refers to prevention of bone loss, especially the inhibition of removal of existing bone either from the mineral phase and/or the organic matrix phase, through direct or indirect alteration of osteoclast formation or metabolism. Thus, the term "inhibitor of bone resorption" as used herein refers to agents that prevent bone loss by the direct or indirect alteration of osteoclast formation or metabolism.

The term "osteogenically effective" means that amount which effects the formation and differentiation of bone. As use herein, an osteogenically effective dose is also "pharmaceutically effective."

The term "subject" as used herein refers to a living vertebrate animal such as a mammal or bird in need of treatment, i.e., in need of bone repair or replacement. Such need arises locally in cases of bone fracture, non-union, defect, prosthesis implantation, and the like. Such need also arises in cases of systemic bone disease, as in osteoporosis, osteoarthritis, Paget's disease, osteomalacia, osteohalisteresis, multiple myeloma and other forms of cancer, and age-related loss of bone mass.

The term "treatment" as used herein shall mean (1) providing a subject with an amount of a substance sufficient to act prophylactically to prevent the development of a weakened and/or unhealthy state; or (2) providing a subject with a sufficient amount of a substance so as to alleviate or eliminate a disease state and/or the symptoms of a disease state, and a weakened and/or unhealthy state.

Any parathyroid hormone (PTH) may be used as the second compound of this invention. The term parathyroid hormone refers to parathyroid hormone, fragments or metabolites thereof and structural analogs thereof which can stimulate bone formation and increase bone mass. Such functional activity is readily determined by those skilled in the art according to standard assays (e.g., see Anabolic Agent Protocol described hereinafter and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below however other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1-34 Treatment of Osteoporosis with Added Hormone Replacement Therapy: Biochemical, Kinetic and Histological Responses" Osteoporosis Int.1:162–170.

PTH 1-34 may be purchased from Bachem of Torrence, Calif.

Drugs which prevent bone loss, and/or add back lost bone and/or increase bone mass may be evaluated in the ovariectomized rat. This animal model is well established in the art (see, for example, Wronski, et al. (1985) Calcif. Tissue Int 37:324–328; Kimmel, et al. (1990) Calcif Tissue Int 46:101–110; and Durbridge, et al. (1990) Calcif. Tissue Int. 47:383–387; these references were hereby incorporated in their entirety). Wronski, et al. ((1985) Calcif. Tissue Int. 43:179–183)) describe the association of bone loss and bone turnover in the ovariectomized rat. Also, Hock et al., describe the use of immature rats ((1988) Endocrinology, Vol. 122, pp. 2899–2904).

PTH and a compound of formula I may be administered sequentially, concurrently, or simultaneously as a single composition to the subject. If administered sequentially, the period between the administration of PTH and a compound of formula I will typically be one week to one year, and optimally, one week to six months. In a preferred administration scheme, the subject will, after administration of PTH, with or without a compound of formula I, be administered a compound of formula I after cessation of administration of PTH.

Pharmaceutical formulations of the invention which include PTH and/or a compound of formula I for administration will generally include an osteogenically effective amount of the bone growth factor to promote bone growth, in addition to a pharmaceutically acceptable excipient. Suitable excipients include most carriers approved for parenteral administration, including water, saline, Ringer's solution, Hank's solution, and solutions of glucose, lactose dextrose, ethanol, glycerol, albumin, and the like. These compositions may optically include stabilizers, antioxidants, antimicrobials, preservatives, buffering agents, surfactants, and other accessory additives. PTH and/or raloxifene may also be delivered in an iontophoretic patch. A thorough discussion of suitable vehicles for parenteral administration may be found in E. W. Martin, "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

If the combination is administered as a single composition, the molar ratio of PTH to a compound of formula I will be about 10:1 to 1:10, preferably, 5:1 to 1:5, and optimally, 1:1. Furthermore, if administered as a single composition, it may be separate components of the composition, or they may be conjugated to each other.

The precise dosage necessary will vary with the age, size, sex and condition of the subject, the nature and severity of the disorder to be treated, and the like; thus, a precise effective amount cannot be specified in advance and will be determined by the care giver. However, appropriate amounts may be determined by routine experimentation with animal models. In general terms, an effective dose of PTH for systemic treatment will range from about 0.001 $\mu$g/kg to about 10 mg/kg of body weight, per day. As effective dose for a compound of formula I is about 10 mg to 40 mg per day.

The methods and compositions of the invention are useful for treating bone fractures, defects, and disorders which result in weakened bones such as osteoporosis, osteoarthritis, Paget's disease, osteohalisteresis, osteomalacia, bone loss resulting from multiple myeloma and other forms of cancer, bone loss resulting from side effects of other medical treatment (such as steroids), and age-related loss of bone mass.

In accordance with one method of use, PTH and a compound of formula I may be administered systemically, orally and/or parenterally, including subcutaneous or intravenous injection, and/or intranasally.

In accordance with another method of use PTH may be administered locally to a specific area in need of bone growth or repair, with the concomitant administration of raloxifene at the site, or the administration of a compound of formula I in a separate vehicle, or, it may be provided locally, with the administration of PTH in a separate vehicle. Thus, the PTH and/or a compound of formula I may be implanted directly at the site to be treated, for example, by injection or surgical implantation. Suitable carriers include hydrogels, controlled- or sustained-release devices (e.g., an Alzet® minipump), polyactic acid, and collagen matrices. Presently preferred carriers are formulations of atelopeptide collagen containing particulate calcium phosphate mineral components, such as combinations of homologous or xenographic fibrillar atelopeptide collagen (for example Zyderm® Collagen Implant, available from Collagen Corporation, Palo Alto, Calif.) with hydroxyapatitetricalcium phosphate (HA-TCP, available from Zimmer, Inc., Warsaw, Ind.).

Dental and orthopedic implants can be coated with PTH in combination with raloxifene, to enhance attachment of the implant device to the bone. Alternatively, PTH can be used to coat the implant, and raloxifene can be administered concomitantly or sequentially in a separate vehicle, and vice versa.

In general, implant devices may be coated with a PTH and/or a compound of formula I as follows. The PTH (and compound of formula I, if desired) is dissolved at a concentration in the range of 0.01 μg/ml to 200 mg/ml in phosphate-buffered saline (PBS) containing 2 mg/ml serum albumin. The porous end of an implant is dipped in the solution and is air dried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing PTH (and a compound of formula I, if desired) is mixed with collagen gel or human collagen (e.g. Zyderm® Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the bony site immediately or is air-dried and rehydrated with PBS prior to implanting, with the objective of maximizing new bone formation into the implant while minimizing the ingrowth of soft tissue into the implant site.

ASSAY

Rats are ovariectomized (OVX) 4 weeks of age and given sc vehicle (v) or hPTH 1-34 (P) at 8 μg/100 g/d alone or in combination with sc compound of formula I (C) at 0.3 mg/100 g/d as follows: V 24d; C 24d; P 24d; P & C 24d; P 12d then V12d; P 12d the C 12d; V12d; the C 12d. Rats are killed on d24, and blood, femurs, lumbar vertebrae and kidneys collected. Bone mass is measured as Ca and dry weight (DW) of distal half femurs; vertebrae are processed for histomorphometry.

Data are corrected per 100 g body weight. Distal half femur Ca and DW decrease in OVX compared to sham rats. Bone mass is increased by the compounds of formula I and by PTH.

We claim:

1. A method for inhibiting conditions which present low bone mass comprising administering to a mammal in need of such inhibition an synergistic effective amount of a compound of formula I

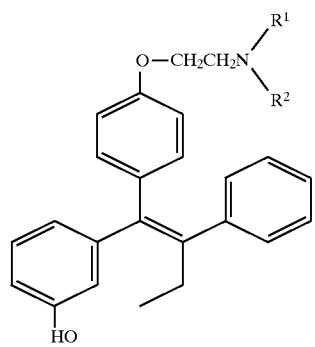

wherein $R^1$ and $R^2$ may be the same of different provided that, when $R^1$ and $R^2$ are the same, each is a methyl or ethyl group, and, when $R^1$ and $R^2$ are different, one of them is a methyl or ethyl group and the other is a hydrogen or a benzyl group; or a pharmaceutically acceptable salt thereof; together with or in combination with an effective amount of parathyroid hormone.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

4. A method as recited in claim 1 wherein the condition which presents with low bone mass is osteoporosis.

5. A method as recited in claim 1 wherein the compound of formula I and parathyroid hormone are administered substantially simultaneously.

6. A method as recited in claim 1 wherein parathyroid hormone is administered for a period of from about three months to about three years.

7. A method as recited in claim 6 followed by administration of a compound of formula I for a period of from about three months to about three years without the administration of parathyroid hormone during the period of from about three months to about three years.

8. A method as recited in claim 6 followed by administration of a compound of formula I for a period greater than about three years without the administration of parathyroid hormone during the greater than about three year period.

9. A pharmaceutical composition comprising an effective amount of a compound of formula I

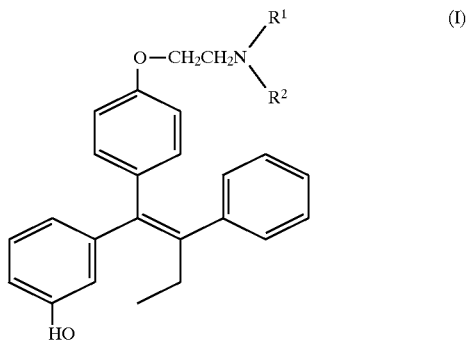

wherein $R^1$ and $R^2$ may be the same of different provided that, when $R^1$ and $R^2$ are the same, each is a methyl or ethyl group, and, when $R^1$ and $R^2$ are different, one of them is a methyl or ethyl group and the other is a halogen or a benzyl group; or a pharmaceutically acceptable salt thereof; and an effective amount of parathyroid hormone.

10. A kit containing a treatment for a condition which presents low bone mass comprising:

A therapeutically synergistic effective amount of a compound of formula I

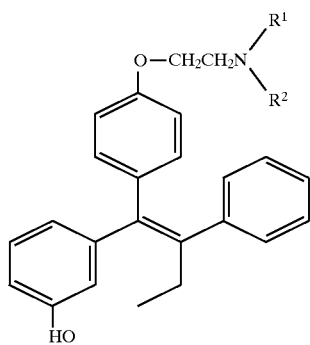

(I)

wherein

R[1] and R[2] may be the same of different provided that, when R[1] and R[2] are the same, each is a methyl or ethyl group, and, when R[1] and R[2] are different, one of them is a methyl or ethyl group and the other is a hydrogen or a benzyl group; or a pharmaceutically acceptable salt thereof; and a pharmaceutically acceptable carrier in a first unit dosage form; a therapeutically effective amount of parathyroid hormone and a pharmaceutically acceptable carrier in a second unit dosage form; and container means for containing said first and second dosage forms.

* * * * *

UNITED STATES PATENT AND TRADEMARK OFFICE
CERTIFICATE OF CORRECTION

PATENT NO.  : 5,861,438
DATED       : January 19, 1999
INVENTOR(S) : David B. MacLean, et al.

It is certified that error appears in the above-identified patent and that said Letters Patent is hereby corrected as shown below:

Column 3, line 11, ")-2-phenylbut-1-ene " should read --(-2-phenylbut-1-ene)--;

Column 4, line 19, " 0.01 mg to 70 mg " should read --.01 mg to 70 mg --;

Column 10, line 34 "(an effective)" should read --(a synergistic effective)--

Signed and Sealed this

Twenty-eighth Day of September, 1999

Attest:

Attesting Officer

Q. TODD DICKINSON

Acting Commissioner of Patents and Trademarks